United States Patent [19]

Commeyras et al.

[11] 3,940,316

[45] Feb. 24, 1976

[54] PROCESS FOR THE PRODUCTION OF ORGANIC ACIDS BY BIOLOGICAL HYDROLYSIS

[75] Inventors: Auguste Commeyras, Clapiers; Alain Arnaud, Clermont L'Herault; Pierre Galzy; Jean-Claude Jallageas, both of Montpellier, all of France

[73] Assignee: Agence Nationale de Valorisation de la Recherche (ANVAR), Neuilly-sur-Seine, France

[22] Filed: Sept. 17, 1974

[21] Appl. No.: 506,717

[30] Foreign Application Priority Data

Sept. 19, 1973 France .......................... 73.33613

[52] U.S. Cl. .................................. 195/50; 195/29
[51] Int. Cl.² .................................... C12D 1/02
[58] Field of Search .......................... 195/29, 50

[56] References Cited
UNITED STATES PATENTS

| | | | |
|---|---|---|---|
| 3,494,831 | 2/1970 | Nakayama et al. | 195/29 |
| 3,668,074 | 6/1972 | Burns | 195/50 |
| 3,730,838 | 5/1973 | Chibata et al. | 195/29 |

*Primary Examiner*—Alvin E. Tanenholtz
*Attorney, Agent, or Firm*—Donald D. Jeffery

[57] ABSTRACT

The present invention relates to a process for the production of organic acids by biologically hydrolysing the corresponding nitriles.

This process is distinguished by the fact that the nitrile in aqueous solution is subjected to the action of bacteria showing nitrilasic activity, preferably selected from the species: *Bacillus, Bacteridium* as defined by Prevot, *Micrococcus* and *Brevibacterium* as defined by Bergey.

The process according to the invention can be used in particular for the production of racemic lactic acid.

10 Claims, No Drawings

PROCESS FOR THE PRODUCTION OF ORGANIC ACIDS BY BIOLOGICAL HYDROLYSIS

BACKGROUND OF INVENTION

It is known that economically important organic acids such as, for example, lactic acid and amino acids in general, can be obtained by subjecting the corresponding nitriles to chemical hydrolysis. However, this process cannot always be applied, especially since certain nitriles are resistant to chemical hydrolysis. In such cases, alternative methods have to be adopted. In the case of α-amino acids for example, it is possible to use hydantoin. Although effective, this method is technologically involved. In other cases, the product of chemical hydrolysis is difficult to separate from the other constituents of the reaction medium.

SUMMARY OF INVENTION

The present invention provides a technically simple process by which it is possible to hydrolyze almost all the nitriles under mild conditions. The process is of particular advantage in cases where delicate compounds are being treated. No difficulties are involved in separating the acid obtained from the reaction medium.

In the process according to the invention, an organic acid is produced from the corresponding nitrile by subjecting that nitrile, in aqueous solution, to the action of bacteria which show nitrilasic activity, and by subsequently separating the bacterial mass from the acid solution. The bacteria showing nitrilasic activity used for the process according to the invention are preferably selected from the species *Bacillus*, *Bacteridium* as defined by Prevot, *Micrococcus* and *Brevibacterium* as defined by Bergey.

More particularly, these bacteria are selected from the strains lodged in the Collection de la Chaire de Genetique de l'Ecole Nationale Superieure Agronomique de Montpellier (France), under the numbers R 332, R 340, R 341, A 111, B 222, A 112, A 13, A 141, A 142, B 211, B 212, B 221, C 211, R 21, R 22, R 311, R 312, R 331, which show the morphological and physiological characteristics described in Tables I and II.

The nitrile solution is preferably adjusted to a slightly basic pH-value, for example with potash or ammonia, before being exposed to the action of the bacteria.

In the process according to the invention, the strains with nitrilasic activity, after culture in a nutrient medium, are suspended in an aqueous solution of the nitrile to be hydrolyzed for a period of a few hours. The pH-value of the solution is kept slightly basic (for example pH 8) or neutral. In some cases, it is necessary in order to complete hydrolysis slightly to acidify the pH-value of the solution after about 1 hour.

On completion of hydrolysis, i.e. generally after a few hours, the bacteria are eliminated by any method known in the science of biology, for example by centrifuging. The acid is extracted from the solution by known methods, for example by extraction or precipitation.

In one preferred embodiment of the invention, hydrolyzed of bacteria with nitrilasic activity are selected by inoculating a medium containing 1.17 % of yeast carbon base Difco, 0.1 % of acetonitrile, 2.5 % of gelose, accommodated in a sterile Petri dish, with various sources of bacteria such as sols, industrial effluents or waste. The colonies formed are isolated, after which the cultures are purified by dilution and spreading over the same medium. The clones thus obtained are then studied.

The strains thus selected may be maintained in a medium containing minerals, ammonia, vitamins and glucose, such as for example glucose-containing yeast nitrogen base Difco.

The nitrilasic activity of the strains selected by the process described above is of a very general nature. Thus, the strains described in this Specification are capable of hydrolysing virtually every one of the following types of compounds:

simple nitriles such as acetonitrile,
α-aminonitriles such as α-aminopropionitrile, α-amino-γ-methyl thiobutyronitrile, α-aminobutyronitrile, aminoacetonitrile,
α-hydroxy nitriles such as lactonitrile, hydroxy acetonitrile,
β-aminonitriles such as amino-3-propionitrile, dinitriles such as malonitrile,
α-unsaturated nitriles such as acrylonitrile,
α-benzonitriles, such as homoveratric nitrile.

By applying the selection process described above, 18 strains were isolated with a level of nitrilasic activity of particular value for carrying out the process. These strains show the following common characteristics:

Gram positive; negative alcohol/acid resistance.
Strict aerobiosis; positive catalase.
Utilisation of glucose, saccharose, maltose and lactose by the oxidative root without gas formation or acidification.
No strain forms alcohol. Starch is not hydrolysed, but there is growth on potato.
Tyrosinase research test on potato: negative. Vitamin demand.
Absence of hydrolysis of gelatin.
Growth in ammonia and on nitrates as sole nitrogen source.
No liberation of hydrogen sulphide.
Absence of growth in the presence of hypersaline broth.
All the strains produce ammonia after culture on nitrates.

In addition, they produce nitrites, except for the strains B 221, B 211, B 212 and C 211. The strain B 222 gives off gases from nitrates.

TABLE I

| | | | MORPHOLOGICAL CHARACTERISTICS | |
| --- | --- | --- | --- | --- |
| Strain | Spore | Mobility | Cellular morphology | Color morphology |
| R 332 | + | low | small rods (1.8–3.6)μ × 0.9μ | Circular, smooth, convex, pink coloured, defined edge |
| R 340 | + | − | small rods 2.7μ × 0.9μ | Circular, small, white, diffuse edge |
| R 341 | + | − | small rods 2.7μ × 0.9μ | Coarse, highly granular, white, flat |
| A 111 | − | − | shells | Circular, small, wrinkled, |

TABLE I-continued

MORPHOLOGICAL CHARACTERISTICS

| Strain | Spore | Mobility | Cellular morphology | Color morphology |
|---|---|---|---|---|
| B 222 | – | + | 0.9 to 1.8μ small rods | convex, pink, lobed edge |
| A 112 | – | low | (3.6–4.5)μ × 0.9μ small rods | Circular, small, orangey yellow in colour |
| A 13 | – | low | (1.8–3.6)μ × 0.9μ small rods | Small, opaque, three-dimensional, lobed edge, orangey pink |
| A 141 | – | – | 2.2μ × 0.9μ small rods | Circular, smooth, opaque, pinkey orange, defined edge |
| A 142 | – | – | (1.8–3.6)μ × 0.9μ small rods | Small, almost flat, opaque, granular, pinkey orange, lobed edge |
| B 211 | – | – | (3.6–4.5)μ × 0.9μ small rods | Circular, smooth, opaque, orange, defined edge |
| B 212 | – | – | 1.8μ × 0.9μ small rods | Circular, dished, small, smooth, pink, defined edge |
| B 221 | – | low | 3.6μ × 0.9μ small rods | Circular, dished, smooth, pink, defined edge |
| C 211 | – | low | (3.6–4)μ × 0.9μ small rods | Circular, heavily lobed, three-dimensional, orangey yellow in colour |
| R 21 | – | – | (3.6–8.1)μ × 0.9μ small rods | Circular, smooth, brilliant, pink, defined edge |
| R 22 | – | low | 5.4μ × 0.9μ small rods | Circular, flat, pink, granular slightly lobed edge |
| R 311 | – | low | 2.7μ × 0.9μ small rods | Circular, smooth, orange, three-dimensional, defined edge |
| R 312 | – | – | (1.8–3.6)μ × 0.9μ small rods | Circular, yellow, three-dimensional, defined edge |
| R 331 | – | – | (4.5–9)μ × 0.9μ small rods | Circular, convex, yellow, defined edge |
|  |  |  | 4.5μ × 0.9μ | Circular, pink, flat, diffuse and opaque |

TABLE II

PRINCIPAL PHYSIOLOGICAL CHARACTERISTICS

| Strain | Oxidase test | Indole | Citric acid utilisation | Hydrolysis of egg white | optimum pH | Production of acetylmethyl carbinol |
|---|---|---|---|---|---|---|
| R 332 | – | – | – | – | 6.5 | high |
| R 340 | – | + | + | – | 6.5 | – |
| R 341 | – | + | – | – | 6.0 | – |
| A 111 | – | + | + | slight | 6.5 | low |
| B 222 | + | – | + | – | 6.0 | – |
| A 112 | – | + | + | – | 6.5 | – |
| A 13 | – | + | – | – | 6.0 | low |
| A 141 | – | – | + | – | 6.5 | low |
| A 142 | – | + | + | – | 6.0 | low |
| B 211 | – | + | + | – | 6.5 | high |
| B 212 | – | – | + | + | 6.0 | – |
| B 221 | – | + | + | – | 6.5 | – |
| C 211 | – | + | – | – | 6.0 | – |
| R 21 | – | + | + | – | 7.5 | – |
| R 22 | – | + | + | – | 6.0 | – |
| R 311 | – | + | + | – | 6.0 | low |
| R 312 | – | – | + | slight | 6.0 | – |
| R 331 | – | + | – | + | 6.0 | – |

The strains C 211, R 312, B 222, A 111, R 341, R 340 and R 332 are lodged at the Centraal Bureau voor Schimmel-cultures (Holland) under the numbers:

C 211 : CBS
R 312 : CBS 717-73
B 222 : CBS
A 111 : CBS
R 341 : CBS
R 340 : CBS
R 332 : CBS

The strain R 332 belongs to the *Bacillus* species, but shows low proteolytic activity. The strains R 340 and R 341 are similar to the *Bacteridium* strain as defined by Prevot. The other strains are asporulated. The strain A 111 is a *Micrococcus*. All the other strains are similar to the *Brevibacterium* species as defined by Bergey. It should be noted that the strain B 222 is very similar to *Brevibacterium imperiale*.

Although, in certain cases (homoveratric nitrile for example), the low solubility of the nitrile in water presents a problem, this does not have any real adverse effect upon the nitrilasic activity of the bacteria suitable for use in the process according to the invention.

One advantage of the process according to the invention is that the bacteria which are still active at the end of the process can be recycled, so that it is possible to a certain extent to carry out the process semicontinuously and to reduce the amount of potash and ammonia required at the beginning of the following reaction.

DESCRIPTION OF PREFERRED EMBODIMENTS

The process according to the invention and certain aspects of its industrial application are described in the following Examples. However, the process according to the invention is by no means restricted to these Examples.

Thus, the strains according to the invention can be cultured on low-cost media, in particular using as carbon-containing culture substrate hexadecanes or gas oils (which enables paraffin to be extracted from gas oils) or even using lactoserum as the complete medium.

These Examples illustrating the application of the process according to the invention were all carried out with the strain R 312 lodged in the Collection de la Chaire de Genetique de l'Ecole Nationale Superieure Agronomique de Montpellier, and also at the Centraal Bureau Voor Schimmelcultures (Holland) under the number CBS 717-73. These Examples are particularly intended to illustrate the non-specificity of the strains selected, and it is for this reason that they were all carried out with the strain R 312, although almost all the strains selected are capable of the hydrolyses described hereinafter.

EXAMPLE 1

Preparation of racemic lactic acid:

The strain R 312 is cultured on a medium containing glucose as carbon source. After culture, the cells are centrifuged, washed with a physiological salt solution and then suspended in the reaction medium consisting of a 10 % by weight solution of lactonitrile obtained by chemical synthesis. The pH-value is adjusted to 8 with potash or ammonia. The bacterial cells, representing approximately 20 to 40 g of dry material per liter, completely hydrolyzed the nitrile over a period of 2 to 3 hours with stirring at a temperature of 25°C. They are then eliminated by centrifuging. The supernatant liquid contains ammonium lactate which can be recovered in a quantitative yield by drying. This product may be used as such, because its applications are numerous, for example as an antiscaling agent in washing solutions. The lactic acid can also be recovered in a quantitative yield by methods known per se. For example, acidification may be followed by continuous extraction with ethyl ether or with any other suitable organic solvent. The lactic acid thus recovered is suitable for use, for example in the food industry and in the chemical or pharmaceutical industry.

EXAMPLE 2

Modification of the process described in Example 1:

In this process, lactonitrile is synthesised in situ by the action of an aqueous acetaldehyde solution on an aqueous solution of hydrocyanic acid in exactly the same molar concentrations as above. The pH-value of the solution is adjusted to approximately 5 by the addition of concentrated ammonia in order to start the reaction. In a second stage, the pH-value of the solution is adjusted to 8 by the addition of ammonia, the bacterial cells are suspended in the medium in a quantity of 20 to 40 g of dry material per liter, and hydrolysis carried out over a period of 2 to 3 hours in the manner described in the preceding Example.

EXAMPLE 3

Preparation of glycine:

As in the preceding Examples, the strain R 312 is cultured on a medium containing glucose as carbon source. After culture, the cells are centrifuged, washed with a physiological salt solution and then suspended in the reaction medium which is a 6 % aqueous solution of glycinonitrile (in hydrochloride form). The pH-value of the solution is adjusted to approximately 8 by adding potash or ammonia.

The bacterial cells, representing from 60 to 80 g of dry material per liter, completely convert the nitrile into acid over a period of about 5 hours at a temperature of 25°C. The pH-value is kept at about 8 for the first hour and at pH 7 for the next 4 hours.

The cells are then eliminated by centrifuging. Glycine is then precipitated from the solution obtained by reducing the solution to 1/5th of its volume and by adding methanol in the absence of heat.

EXAMPLE 4

Preparation of racemic α-alanine:

The strain R 312 is cultured on a medium containing glucose as carbon source. After culture, the cells are centrifuged, washed with a physiological salt solution and then suspended in a reaction medium consisting of a 5 % by weight aqueous solution of α-aminopropionitrile hydrochloride. The pH-value is adjusted to 8 and kept at that level for 2 hours. The bacterial cells, representing 20 to 40 g of dry material per liter, completely hydrolyze the solution over a period of 2 to 3 hours with stirring at a temperature of 25°C. After the cells have been eliminated by centrifuging, the solution contains approximately 40 g of α-alanine per liter which is recovered by known techniques.

EXAMPLE 5

Preparation of β-alanine:

The strain R 312 is cultured and recovered in the same way as described above. It is suspended in a reaction medium consisting of a 5% by weight aqueous solution of amino-3-propionitrile. The pH-value is adjusted to 8 and is kept at that level for 30 minutes. The pH-value is then reduced to 7 and kept at that value for 5 hours with stirring at a temperature of 25°C. The bacterial cells, representing 60 to 80 g of dry material per liter, completely hydrolyze the solution under these conditions. After the cells have been eliminated by centrifuging, the solution contains approximately 60 g per liter of β-alanine which is recovered by known techniques.

EXAMPLE 6

Preparation of racemic methionine:

The strain R 312 is cultured and recovered in the same was as described above. It is suspended in a reaction medium consisting of a 6 % by weight solution in water of α-amino-γ-methyl thiobutyronitrile sulphate. The pH-value is adjusted to 8. The bacterial cells, representing 20 to 40 g of dry material per liter, completely hydrolyze the solution after 3 hours with stirring at a temperature of 25°C. After the cells had been eliminated by centrifuging, the solution is reduced to 1/3rd of its volume and adjusted to pH 7. The methionine precipitates. The yield is of the order of 80%.

EXAMPLE 7

As in Example 2, α-amino-γ-methyl thiobutyronitrile can be prepared in situ from methylmercapto propion aldehyde, ammonia and alkali cyanide used in stoichiometric proportions. On completion of the reaction, the bacteria are suspended. The further procedure is then as in Example 6.

Some remarks should be made on the reaction equilibria prevailing in view of the toxicity of the cyanides.

In cases where hydrolyzed nitrile participates in an equilibrium with hydrocyanic acid:

On the one hand, the constants measured are very favorable to the nitrile in every case.

On the other hand, the hydrolysis reaction displaces the equilibrium towards the disappearance and complete utilisation of the cyanide present in the medium. Nevertheless, the concentration of cyanide in the starting products has to be finally checked in order to avoid any accidents (unfavorable stoichiometric proportions at the outset always being possible).

Accordingly, it is possible by this process to hydrolyzed a large number of nitriles under mild conditions from a simple reaction medium, and to obtain extremely pure compounds in substantially quantitative yields.

What is claimed is:

1. A process for preparing an organic acid by hydrolyzing the corresponding nitrile comprised of (a) suspending bacteria showing nitrilasic activity in a solution containing nitrile, (b) hydrolyzing said nitrile with said bacteria to form the organic acid, and (c) recovering said organic acid from said solution.

2. The process as defined in claim 1 wherein said bacteria is selected from the group consisting of *Bacillus*, *Micrococcus* and *Brevibacterium* as defined by Bergey.

3. The process as defined in claim 2 wherein said bacteria is selected from the group consisting of the strains numbers R 332, R 340, R 341, A 111, B 222, A 112, A 13, A 141, A 142, B 211, B 212, B 221, C 211, R 21, R 22, R 311, R 312 and R 331, deposited at the Chaire de Genetique de l'Ecole Nationale Superieure Agronomique de Montpellier.

4. The process as defined in claim 3 wherein said bacteria is bacteria R 312 deposited in Centraal Bureau voor Schimmelcultures under the number 717.73.

5. The process as defined in claim 1 wherein said bacteria is a bacteria which grows on a medium containing 1.17% of yeast carbon base Difco, 0.1% of acetonitrile and 2.5% of gelose.

6. The process as defined in claim 1 wherein said hydrolysis is carried out at a substantially constant $p_H$ value.

7. The process as defined in claim 6 wherein said $p_H$ value is between 6 and 8.

8. The process as defined in claim 1 wherein said hydrolysis is further characterized by acidifying said solution to complete said hydrolysis before recovery of said organic acid.

9. The process as defined in claim 8 wherein said bacteria is suspended in said solution at a $p_H$ of about 8 and said completion of hydrolysis is carried out at a $p_H$ of about 7.

10. The process as defined in the claim 1 wherein said recovery is affected by centrifuging said solution.

* * * * *